United States Patent [19]
Al-Hassan

[11] Patent Number: 5,912,018
[45] Date of Patent: Jun. 15, 1999

[54] METHODS FOR TREATMENT OF MUSCLE SPASM, EDEMA AND DERMATOLOGICAL CONDITIONS USING EPIDERMAL GEL SECRETION FROM AN ARABIAN GULF CATFISH

[76] Inventor: Jassim M. Al-Hassan, Kuwait University, Faculty of Science, Biochemistry Dept., P.O. Box 5969, 13060, Safat, Kuwait

[21] Appl. No.: 08/905,968

[22] Filed: Aug. 5, 1997

[51] Int. Cl.$^6$ .......................... A61K 35/24; A61K 35/12; A61K 35/60
[52] U.S. Cl. .......................... 424/537; 424/520; 424/571; 424/572; 424/574; 424/523; 514/860-864; 514/817; 514/870; 514/871
[58] Field of Search ...................................... 424/520, 537, 424/571, 572, 574; 514/860–864, 817, 870–871

[56] References Cited

U.S. PATENT DOCUMENTS 5,658,594  8/1997  Al-Hassan ................................ 424/537

OTHER PUBLICATIONS

Al–Hassan, J.M. Int. J. Tiss. Reac. vol. XII, No. 2, pp. 121–135, 1990.

Al–Hassan et al. J. Wilderness Med. vol. 2, No. 3, pp. 153–163, abstract enclosed, 1991.

Al–Hassan et al. Mar. Biol. vol. 88, No. 2, pp. 117–124, abstract enclosed, 1985.

*Primary Examiner*—Leon B. Lankford, Jr.
*Assistant Examiner*—Christopher R. Tate
*Attorney, Agent, or Firm*—Pillsbury Madison & Sutro LLP

[57] ABSTRACT

The present invention provides an epidermal gel secretion of Arabian Gulf catfish which is useful in enhancing wound healing, alleviating muscle spasms and pain, and treating dermatological disorders.

6 Claims, No Drawings

METHODS FOR TREATMENT OF MUSCLE SPASM, EDEMA AND DERMATOLOGICAL CONDITIONS USING EPIDERMAL GEL SECRETION FROM AN ARABIAN GULF CATFISH

FIELD OF THE INVENTION

The present invention relates to the collection, preparation and application of materials which, when applied to wounds in animals, such as mammals, reduces healing times. The compositions of the present invention reduce muscle spasms and post-operative pain associated with disc surgery. Moreover, the compositions of the present invention reduce pain in the joints due to, for example, edema. The compositions of the present invention have also been useful in treating dermatological conditions, such as some types of eczema and psoriasis. The present invention provides therefore, methods of treating each of these conditions.

BACKGROUND OF THE INVENTION

Wound repair in animals follows a well defined time coverage of sequential events, starting with clot formation and culminating with integration of newly synthesized cells and matrix components into the damaged tissue area. The time course of major events in the wound healing process has been described in the studies from many laboratories. Healing in most "normal" cases is essentially complete in approximately 10 days. However, a number of circumstances can greatly extend this time, including infections, nutritional deficiencies, metabolic conditions such as diabetes, genetic defects, such as blood clotting factor deficiencies, and advanced age of the victim.

Many procedures and/or applications have been proposed to enhance healing rates. Antimicrobial agents help healing by blocking infections, but these may, in some instances, also interfere with cellular processes required for wound healing and cause some retardation of rates. Mechanical procedures to insure wound closure, including suturing or bandaging may speed recovery and help prevent excess scar tissue deposition. Chemical treatments with potential stimulatory action on various of the wound healing steps have been utilized with some success, but individual chemical or biochemical agents may be expected to have modes of action on only a limited number of processes within the complex scheme of wound healing reactions, without necessarily stimulating the total process. A number of synthetic or naturally occurring mixtures of components have been proposed in the past to contain a mixture of constituents which are generally stimulatory to the healing process. Convincing evidence supporting these claims and scientific evidence suggesting a physiological basis for the proposed stimulations are lacking.

U.S. Pat. No. 4,296,099 discloses a process for extracting embryonic calf skin which comprises initially grinding the calf skin, extracting same, and separating the resulting extract and lyophilizing the separated extract to provide an extract which exhibits cicatrisive activity and that is employed in cosmetic and pharmaceutical compositions.

Al-Hassan et al (*Marine Biology* 70, 29–33 (1982)) describe the collection of copious amounts of proteinaceous gel from the epidermal cells of Arabian Gulf catfish (*Arius thalassinus*, subsequently corrected to *Arius bilineatus*) when the fish are threatened or injured. Some of the proteins are reported to exist as high molecular weight aggregates. Proteins of 18,000 mol. wt. and 44,000 to 45,000 mol. wt. are prevalent in the gel secretion. The gel is reported to contain several lytic enzyme activities which resemble those of some animal venoms.

Thulesius et al. (*Gen. Pharmac.* 14: 129–132 (1983)) have reported that both the venom and gel of *Arius thalasinus* (subsequently corrected to *Arius bilineatus*) have a large number of protein components with several enzymatic activities which resemble other complex venoms and include esterases, phosphatases and active hemolytic components. Preparations of the gland venom were found to cause contraction of smooth muscle in human umbilical artery and include depressor response in vivo.

The proteinaceous toxin secreted by the epidermal cells of the Arabian Gulf catfish or "skin toxin" was found to produce respiratory distress, agitated behaviors and increased heart rate in rabbits, with an $LD_{50}$ of about 1.5 mg protein/kg body weight (Al-Hassan et al. *Toxicon.* 23(3) 532–534 (1985)). The skin toxin has also been found to cause contraction of sheep renal artery, as well as arteries from other tissues and species (Al-Hassan et al., *Toxicon* 24 (10): 1009–1014 (1986)). At least two components of the skin toxin have been identified. One component has been described as having acetylcholine-like action which is heat stable and not inactivated by trypsin; possibly being a low molecular weight non-protein component. The activity of the second factor appears to be dependent on prostaglandin synthesis and causes release of prostaglandins from arterial preparations during contraction.

The epidermal gel secretions of *Arius thalassinus* (subsequently corrected to *Arius bilineatus*) have also been found, at 4 fold dilution, to inhibit *Streptococcus faecalis, Staphylococcus pyogenes, Shigella flexnen,* and *Saccharomyces cervisiae,* thus demonstrating moderate antibacterial activity (Al-Hassan et al., *J. Toxicol.—Toxin Reviews* 6(1): 1–43 (1987)).

At present, four species of catfish are known to be present in the Gulf: *Arius thalassinus, Arius dussumieri, Arius tenuispinis* and *Arius bilineatus* (Al-Hassan et al., *J. Nat. Hist.* 22, 473–487 (1988)). Although the initial studies leading to the present invention were carried out on fish identified as *Arius thalassinus,* the species used has been reclassified as *Arius bilineatus.* Unless otherwise noted, specific examples set forth in the present application refer to *Arius bilineatus.*

SUMMARY OF THE INVENTION

The present invention provides a preparation or composition from the epidermis of fish particularly catfish and more particularly from Ariid catfish, such as *Arius thalassinus* and *Arius bilineatus,* that can be safely applied to the wound of an animal or human and that will stimulate wound healing.

The compositions of the present invention are also useful in treating muscle spasms, back pain, post-operative pain associated with disc surgery, dermatological conditions and painful joints.

Other objects of the present invention are to provide a method of collecting materials from the epidermis of fish. Still other objects are to provide a method of processing materials collected from an epidermis of a fish to make the same suitable and safe for the above-described uses.

Principal features of the invention include the shocking of the fish to stimulate the release of epidermal materials and in particular filamentous protein coils from the club cells which form a portion of the cellular structure of the fish epidermis.

Other features include the collection of the epidermal materials from the fish and the processing, including sterilization, of the collected secretions to make the preparations safe and viable for the uses described herein.

Additional objects and features of the invention will become apparent to those skilled in the pertinent art from the following detailed description.

DETAILED DESCRIPTION OF THE INVENTION

It has been found that the application of certain fish epidermal preparations to wounds appears to act quite generally in stimulating all observed phases of the healing process. The complex mixture of pharmacologically active components in the preparation thus appears to contain a balanced combination of stimulatory agents which influence the entire healing process. This is supported by both histological and biochemical observations. Many of the active constituents of the preparation have now been isolated and their modes, of action in healing have been documented. These provide a clear indication of how the preparation can function to stimulate healing.

It has been observed that Ariid catfish, when threatened or injured or otherwise shocked, secrete a proteinaceous, gel-like mixture from unicellular glands, which are frequently termed club cells. This material, together with some additional epidermal components, is collected by gentle mechanical scraping, or suction, from the epidermal surfaces after washing the living fish thoroughly with sea water to remove contaminants of blood, spine venom or waste material from its anal pore. The collected material has a gel-like consistency and will be referred to herein as epidermal gel. The gel is preferably immediately frozen in dry ice or liquid nitrogen to limit microbial growth. The total gel preparation may be used for application to wounds, but further fractionation and purification of components (proteins and lipids) is commonly employed to provide a safer, more viable preparation for use on wounds.

The dry gel contains 85% protein components and 13% lipids, of its dry weight. Fractionation of the gel components follows two main approaches.
1. Lipid extraction and fractionation If lipids are to be separated then the gel material is lyophilized and then repeatedly extracted with chloroform-:methanol mixture (2:1, v/v). The lipids are then dried by evaporating the organic solvent mixture using a rotary evaporator at room temperature and stored under vacuum in a dark desicator, or under nitrogen in a dark container. The lipids can then be fractionated into polar and non-polar lipids by the use of silica gel column chromatography and the appropriate solvents. The lipids may be used to enrich the preparation either by the addition of total lipids to the total gel or by addition of the desired fraction of the lipid to the total gel preparation or any fraction of the gel.
2. Fractionation of the protein components.

The total gel is homogenized with 25% of its volume of sodium chloride (0.60 M NaCl) or with 25% of its volume of filtered sea water. The resulting homogenate is centrifuged at 105,000 g for 30 min. to obtain two fractions, the soluble and the insoluble fraction. Proteins in both fractions contain biochemical activities related to the wound healing properties of the invention. The insoluble gel can only be fractionated further with difficulty, using chemicals which render it unsuitable for medical applications. The soluble fraction can be fractionated further by using an ammonium sulphate fractionation procedure, followed by a suitable purification method. The individual proteins in the soluble fraction can be separated using any or a combination of the standard protein separation and purification procedures, so as to be used in the pure form, or to be added to the starting gel material for enrichment. The starting gel material or any of its fractions can also be enriched with the total lipids or lipid fractions to enhance the desired activities for a particular application.

The total gel preparation or the further fractionated sample may be referred to as the active component of the present invention.

Shocking the fish may be accomplished by thermal shock, physical abrasions, neural stimulation or towing the fish through the water with the fishing hook still in its mouth.

The catfish as well as many additional fish species, for example Indian major carp Catla Catla, the fresh water fish species *Clarias batrachus, Heteropheustes fossilis* (Block). *Corydoras aeneus* and eels, have club cells in their epidermal layers. Epidermal preparations from these other species will contain some components that resemble those elaborated by the epidermis of Ariid catfish secretions in their biochemical and pharmacological properties, but these may be more difficult to obtain in a form separated from the bulk of the epidermal materials. Those other fish can however, still be used as source material for collection of components with similar action to the wound healing preparations described herein by homogenization and extraction of the epidermal materials.

Fractionation and purification of a soluble fraction of the Ariid epidermal gel is by homogenization of the total gel with dilute saline, followed by centrifugation. The soluble gel fraction is sterilized by membrane filtration or ultrasound treatment. Soluble protein fractions may be stored either frozen, preferably at −80° C., or for shorter periods, at 0° to 5° C. Soluble gel fractions may be applied directly to wounds to enhance healing.

The soluble gel may be fractionated further to yield active proteins and lipids which have effects on wound healing as described below. These are active individually in enhancing various steps of the wound healing processes. They may be recombined to reconstitute general activity. Some of these components have been isolated and characterized, including a hemolytic factor, a hemagglutination factor (lectin), a clotting factor, platelet activating factors, esterases and a phosphatase.

A summary of some active constituents of soluble gel which have been identified, to date, as affecting specific healing characteristics as identified below (A through H) is as follows:
A. Clotting Factor A high molecular weight (500,000) protein catalyzes conversion of blood clotting Factor X to Xa (Summers et al., *Fed. Proc.* 44:1844 (1985)). Active Factor Xa then catalyzes production of thrombin and subsequently the formation of the fibrin clot. The soluble gel clotting factor is a calcium dependent serine protease with specificity similar to that of normal blood proteases causing activation of Factor X.
B. Lectin A galactose specific lectin protein (200,000 molecular weight) accounts for about 2% of the soluble protein (Al-Hassan et al., *Comp. Biochem. Physiol.* 85B:31–37 (1986)). This protein causes agglutination of human types A, B, and O red blood cells. It is capable of recognition of galactose moieties on the surface of cells and may aid in wound closure and adhesion of injured surfaces.
C. Lytic Enzymes The gel contains a number of hydrolytic components (Al-Hassan et al., *J. Toxicol.—Toxin.* Rev. 6: 1–43 (1987)). There is an active hemolytic protein which induces lysis of red blood cells. Proteolytic activity is very low in the crude preparation, but is noted in partially purified preparation, indicating removal of endogenous protease inhibitors. There are at least four esterases present in the preparation. Phosphatase activity is also present. No lipase activity is measurable.

D. Phosphorylases

A family of phosphorylases is present in the soluble gel protein mixture (Criddle et al., *FASEB J.* 2:A995 (1988)). These include (a) a tyrosine phosphorylase, (b) phosphorylase(s) which appear to generally phosphorylate many of the gel proteins or added plasma membrane proteins at serine, threonine and tyrosine residues, and (c) an enzyme which phosphorylates phosphatidyl inositol.

E. Platelet Activating Factors

The epidermal preparation contains a family of 1-O-alkyl-2-acetyl-sn-glycero-3-phosphorylcholine molecules, with alkyl chain lengths varying from 15 to 24 carbons, which stimulate activation of platelets (Summers et al. *Biochem. Biophys. Acta* 1091:329–336 (1991)). These are present at levels 5000 times those commonly found in animal sources.

F. Prostaglandins

The epidermal preparation contains at least two components which stimulate contraction of smooth muscle (Al-Hassan et al., *Prostaglandins, Leukotrienes and Medicine* 28: 95–102 (1987)). One is blocked by cyclooxigenase inhibitors, and the other by atropine.

G. Macrophage Growth Factor

The epidermal secretions contain a macrophage growth factor. This factor attracts macrophages to the wound site and induces their proliferation. These cells play an essential role in wound healing through their action as the early immune cells that invade the wound area, attack the damaged and foreign cells, and secrete chemoattractants for the next line of cells to be involved in the wound healing processes.

H. Other Activities

The epidermal secretion contains a factor which activates phospholipase $A_2$ (Al-Hassan et al., *J. Toxicol.—Toxin Rev.* 6: 1–43 (1987)). Preparations from the epidermal secretions showed enhanced cellularity and healing of wounds in test animals (Al-Hassan et al., *J. Wilderness Med.* 2:153–163 (1991)), acceleration of wound healing in man (Al-Hassan et al., *The Lancet,* Vol. 1 for 1983; 1043–1044), enhanced healing of diabetic foot ulcers and antiedemic activity when applied to wounds and ulcers (Al-Hassan, *Int. J. of Tissue reactions XII* (2), 121–135 (1990)). It also stimulates vascular permeability when injected intradermally in rat skin, indicating that the preparations may facilitate the wound healing process through their action on capillaries and the associated release of neutrophils amongst other wound healing activities.

The benefits of an externally added clotting factor in aiding wound healing are readily apparent. The first step in wound healing is clotting. Clot formation initiates a number of important metabolic events which stimulate cell metabolism and initiate cell proliferation. Primary among these is platelet activation. The high level of platelet activating factors found in the epidermal preparation also rapidly induces platelet activation in the wound area. Among the results of this activation are secretion from the platelets of serotonin, platelet derived growth factors, and other biochemicals. Serotonin aids in vasoconstriction, shutting down the flow of blood to the wound area. Platelet derived growth factor (PDGF) is both chemotactic and mitogenic for fibroblasts, thus it aids in promoting the movement of these collagen producing cells into the wound area and induces their proliferation. The products of the fibroblasts are major components needed for tissue repair. Platelet activation also stimulates hydrolysis of phospholipids and release of inositol phosphates. These inositol compounds regulate calcium levels in the cells and alter cell metabolism.

Phosphorylase action directed by the epidermal preparation has stimulatory activity at several levels in cell metabolism. Direct phosphorylation of phosphatidyl inositol to the di- and triphosphate forms stimulates as described above. In addition, an endogenous inhibitor protein of phospholipase A2 in epidermal membranes is phosphorylated, resulting in deactivation of the inhibitor and expression of the lipase activity. The lipase catalyzes release of arachidonic acid. Arachidonic acid is rapidly converted to prostaglandins which regulate many cellular processes in the wound area. For example, prostaglandins affect inflammatory responses, pain responses, migration of cells into the wound area, angiogenesis and rates of cell proliferation. All these processes are key steps in wound healing.

Lytic enzymes from the epidermal secretion may play important roles in break down of damaged cells. No definite role has yet been established for the lectin present in the epidermal secretion. Lectins have, in general, been postulated to serve as important elements in cellular adhesion. The epidermal gel preparation has been found to promote rapid adhesion of wound tissues. The lectin is a likely candidate for this action as it may recognize and bind galactose moieties on adjacent cell surfaces to give the noted adhesion.

The present invention also provides a method of treating pain and inflammation, including the treatment of muscle (smooth and skeletal) spasms and associated pain, soreness and tightness of muscles in mammalian organisms, such as humans. The method involves applying a muscle pain alleviating effective amount of a composition containing the epidermal gel secretion of the present invention to a mammal in need of such treatment. In this method therefore, the composition of the present invention is a muscle relaxant useful for the treatment of muscle spasms, and associated muscle pain, soreness and tightness of smooth and/or skeletal muscle spasms due to muscle strains, overexertion and minor injuries of, for example, lower and upper back (lumbar and cervical).

In this embodiment of the present invention, a method is provided of eliciting the onset or hastening or enhancing the response for the treatment of pain and inflammation and the treatment of muscle spasm and associated symptoms in a mammalian organism in need of such treatment, involving administering to the organism an analgesically and anti-inflammatory effective amount of the gel secretion of the present invention.

Mammalian or mammalian organism include, but are not limited to, man, dog, cat, horse and cow.

Treatment encompasses the complete range of therapeutically positive effects associated with pharmaceutical medications including reductions of, alleviation of and relief from symptoms or illness which affect the organism.

The amount of preparation (gel material) useful as a muscle relaxant, in the practice of the present invention is preferably about 3 mm thickness of the gel preparation applied over the entire area of the source of lower back pain (lumbar vertebrae and the skeletal muscles next to them on either side of ther vertebral column (about 20 cm in diameter) and/or (upper back pain) to cover an area of a diameter of approximately 15 cm. Persons of skill in the art will appreciate that the amount can vary and will be determined by routine experimentation in many cases.

In another embodiment, the present invention provides a method of treating joint pain due to, for example, edema. In this embodiment, a joint pain alleviating effective amount of a composition containing the epidermal gel secretion of the present invention is applied to a mammal in need of such treatment.

For knee, elbow and other joints, the amount of gel preparation useful as pain alleviator in the practice of the present invention is about 3 mm thickness of material applied to cover the entire area where pain is felt.

For back pain, joint pain or akeletal muscle spasm, the preparation should be applied and covered with a nonabsorbing dressing such as Wet Geliperm wound dressing or transparent food wrapping material (cellophane, etc.), and left for 8 hours. After that, the patient can wash the treated area and resume normal activities. The process can be repeated once every 24 hours for 3–5 days, as the case may require. Some patients might require one application only. The material should be applied while the patient is resting in bed.

In a further embodiment, the present invention provides a method of treating dermatological disorders, such as psoriasis, eczema, seborrheic dermatitis, primary irritant contact dermatitis, allergic contact dermatitis, lamellar ichthyosis, epidermolytic hyperkeratosis, mange and psoriatic arthritis. In this embodiment, the method of the invention involves applying a dermatologically treating effective amount of a composition containing the epidermal gel secretion of the present invention to a mammal in need of such treatment.

The amount of gel secretion useful as a dermatologically effective amount in the practice of the present invention may also vary, with the preferred amount in the range of about 3 mm thickness per affected area.

The composition containing the gel secretion disclosed herein is generally administered topically, and may be formulated using well-known and readily available ingredients. In making the composition of the present invention or any of its fractions, the active ingredient or gel secretion may be mixed with a carrier, or diluted by a carrier, or enclosed within a carrier which may be in the form of a capsule, sachet, paper or other container. When the container serves as a diluent, it may be in a solid, semi-solid or liquid material which acts as a vehicle, excipient or medium for the active ingredient.

The compositions can be in the form of tablets, pills, powders, sachets, cachets, elixirs, suspensions, emulsions, solutions, syrups, aerosols, ointments, foams, aqueous gels or salves containing, for example, up to 98% by weight of the active component(s).

Some examples of suitable carriers, excipient and diluents include, but are not limited to, lactose, dextrose, sucrose, sorbitol, mannitol, starches, gum, acacia, calcium phosphate, alginates, gelatin, calcium silicate, microcrystalline cellulose, polyvinylpyrrolidone, cellulose, water, methyl cellulose, methyl and propyl hydroxybenzoates, talc, magnesium stearate, olive oil, freeze dried filtered sea water and mineral oil.

The formulations can additionally contain lubricating agents, wetting agents, penetrating agents, emulsifying agents, suspending agents, coloring agents and/or perfumes. Compositions of the invention may be formulated so as to provide rapid, sustained or delayed release of the active ingredient after administration, by means known in the art.

Although a preferred form of the invention has been herein described, it is to be understood that the present disclosure is by way of example and that variations are possible without departing from the subject matter described within the scope of the present disclosed invention, including the claims, which subject matter is regarded as the applicant's invention.

All published materials cited herein are hereby incorporated in their entirety by reference.

I claim:

1. A method of treating muscle pain, back pain and joint pain comprising topically administering a muscle pain alleviating effective amount of a composition comprising a sterilized epidermal gel secretion from an Arabian Gulf catfish or a fraction of said secretion to a mammal in need of said treatment.

2. A method of treating edema comprising topically administering an edema alleviating effective amount of a composition comprising a sterilized epidermal gel secretion from an Arabian Gulf catfish or a fraction of said secretion to a mammal in need of said treatment.

3. A method of treating a dermatological disorder selected from the group consisting of psoriasis, eczema, seborrheic dermatitis, primary irritant contact dermatitis, allergic contact dermatitis, lamellar ichthyosis, epidermolytic hyperkeratosis, mange and psoriatic arthritis, said method comprising topically administering a dermatologically effective amount of a composition comprising a sterilized epidermal gel secretion from an Arabian Gulf catfish or a fraction of said secretion to a mammal in need of said treatment.

4. The method of claim 1 wherein said catfish is selected from the group consisting of *Arius thalassinus, Arius bilineatus, Arius dussumieri* and *Arius tenuispinis*.

5. The method of claim 2 wherein said catfish is selected from the group consisting of *Arius thalassinus, Arius bilineatus, Arius dussumieri* and *Arius tenuispinis*.

6. The method of claim 3 wherein said catfish is selected from the group consisting of *Arius thalassinus, Arius bilineatus, Arius dussumieri* and *Arius tenuispinis*.

* * * * *